US010422745B2

(12) United States Patent
Suzuki et al.

(10) Patent No.: US 10,422,745 B2
(45) Date of Patent: Sep. 24, 2019

(54) SCATTERING ABSORBER MEASUREMENT DEVICE AND SCATTERING ABSORBER MEASUREMENT METHOD

(71) Applicant: HAMAMATSU PHOTONICS K.K., Hamamatsu-shi, Shizuoka (JP)

(72) Inventors: Hiroaki Suzuki, Hamamatsu (JP); Motoki Oda, Hamamatsu (JP); Toshihiko Suzuki, Hamamatsu (JP); Etsuko Yamaki, Hamamatsu (JP); Shu Homma, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/738,341

(22) PCT Filed: Jun. 24, 2015

(86) PCT No.: PCT/JP2015/068253
§ 371 (c)(1),
(2) Date: Dec. 20, 2017

(87) PCT Pub. No.: WO2016/208010
PCT Pub. Date: Dec. 29, 2016

(65) Prior Publication Data
US 2018/0180539 A1 Jun. 28, 2018

(51) Int. Cl.
*G01N 21/49* (2006.01)
*G01N 21/17* (2006.01)
(Continued)

(52) U.S. Cl.
CPC ............ *G01N 21/49* (2013.01); *G01N 21/17* (2013.01); *G01N 21/27* (2013.01); *G01N 21/359* (2013.01);
(Continued)

(58) Field of Classification Search
CPC ........ G01N 21/49; G01N 21/17; G01N 21/27; G01N 21/359; G01N 21/4738; G01N 2021/4742
See application file for complete search history.

(56) References Cited

U.S. PATENT DOCUMENTS

2004/0032592 A1  2/2004  Venugopal et al.
2007/0241289 A1  10/2007  Fung et al.

FOREIGN PATENT DOCUMENTS

JP  H11-287755 A  10/1999
JP  2000-146828 A  5/2000
(Continued)

OTHER PUBLICATIONS

Suzuki H et al, "Hemodynamic measurements in deep brain tissues of humans by near-infrared time-resolved spectroscopy", Proc. SPIE 8982, Optical Techniques in Neurosurgery, Neurophotonics, and Optogenetics, vol. 8928, Mar. 5, 2014, p. 892800-1-p. 892800-7, XP060033239.
(Continued)

*Primary Examiner* — Hina F Ayub
(74) *Attorney, Agent, or Firm* — Drinker Biddle & Reath LLP

(57) ABSTRACT

A scattering absorber measurement device includes a light source for outputting a plurality of light pulses having different wavelengths input to a scattering absorber, a photodetector for detecting each light pulse propagating inside the scattering absorber and output a detection signal, and a computation unit for calculating a reduced scattering coefficient and an absorption coefficient according to a time-resolved spectroscopic measurement method on the basis of the detection signal. The computation unit determines data related to a ratio of reduced scattering coefficients among wavelengths of the plurality of light pulses and calculates the reduced scattering coefficient and the absorption coeffi-
(Continued)

cient on the basis of a time-resolved measurement profile of each wavelength based on the detection signal and the data related to the ratio.

6 Claims, 12 Drawing Sheets

(51) Int. Cl.
  *G01N 21/27* (2006.01)
  *G01N 21/47* (2006.01)
  *G01N 21/359* (2014.01)

(52) U.S. Cl.
  CPC . *G01N 21/4738* (2013.01); *G01N 2021/4742* (2013.01)

(56) References Cited

FOREIGN PATENT DOCUMENTS

| | | |
|---|---|---|
| JP | 2006-521869 A | 9/2006 |
| JP | 2015-125090 A | 7/2015 |
| WO | WO-2004/086965 A1 | 10/2004 |

OTHER PUBLICATIONS

Swartling J et al, "Rigorous characterization of time-resolved diffuse spectroscopy systems for measurements of absorption and scattering properties using solid phantoms", Proc. SPIE 5138, Photon Migration and Diffuse-Light Imaging, vol. 5138, Oct. 15, 2003, p. 80-p. 87, XP055522685.
International Preliminary Report on Patentability dated Jan. 4, 2018 for PCT/JP2015/068253.
Cubeddu, Rinald, et al., "Breast lesion characterization by a novel nonlinear perturbation approach," Proc. of SPIE, 2003 vol. 5138, pp. 23-28.
C. D'Andrea et al., "Time-resolved spectrally constrained method for the quantification of chromophore concentrations and scattering parameters in diffusing media," Optics Express, vol. 14, No. 5, Mar. 6, 2006, pp. 1888-1898.
Patterson, Michael S., et al., "Time resolved reflectance and transmittance for the non-invasive measurement of tissue optical properties," Applied Optics vol. 28, No. 12, 1989, pp. 2331-2336.
Sun, Meixiu, et al., "Non-invasive measurement of blood glucose level by time-resolved transmission spectroscopy: A feasibility study," Optics Communications, 2012 vol. 285, pp. 1608-1612.

*Fig.5*

|  | REDUCED SCATTERING COEFFICIENT [1/cm] | | |
|---|---|---|---|
|  | 759nm | 793nm | 834nm |
| COMPARATIVE EXAMPLE | 10.632 | 10.271 | 9.912 |
| SCATTERING COEFFICIENT RATIO (COMPARATIVE EXAMPLE) | 1.0351 | 1.0000 | 0.9650 |
| PRESENT EMBODIMENT | 10.664 | 10.287 | 9.871 |
| SCATTERING COEFFICIENT RATIO (PRESENT EMBODIMENT) | 1.0366 | 1.0000 | 0.9596 |

| | ABSORPTION COEFFICIENT [1/cm] | | |
|---|---|---|---|
| | 760nm | 800nm | 830nm |
| COMPARATIVE EXAMPLE | 0.1515±0.0007 | 0.1424±0.0008 | 0.1598±0.0014 |
| PRESENT EMBODIMENT | 0.1516±0.0006 | 0.1427±0.0007 | 0.1589±0.0009 |

(b)

| | SCATTERING COEFFICIENT [1/cm] | | |
|---|---|---|---|
| | 760nm | 800nm | 830nm |
| COMPARATIVE EXAMPLE | 10.632±0.041 | 10.271±0.039 | 9.912±0.035 |
| PRESENT EMBODIMENT | 10.664±0.014 | 10.287±0.014 | 9.871±0.013 |

(c)

| | AMOUNT OF HEMOGLOBIN | | | |
|---|---|---|---|---|
| | $HbO_2$ | Hb | tHb | $SO_2$ |
| COMPARATIVE EXAMPLE | 43.57±0.66 | 19.56±0.34 | 63.13±0.39 | 69.02±0.68 |
| PRESENT EMBODIMENT | 43.09±0.49 | 19.91±0.25 | 63.00±0.33 | 68.40±0.48 |

Fig.7

| VARIATION COEFFICIENT | ABSORPTION COEFFICIENT [1/cm] | | | SCATTERING COEFFICIENT [1/cm] | | | AMOUNT OF HEMOGLOBIN | |
|---|---|---|---|---|---|---|---|---|
| | 760nm | 800nm | 830nm | 760nm | 800nm | 830nm | tHb [µM] | SO2 [%] |
| 100ms | 10.1% | 6.0% | 8.9% | 5.3% | 4.2% | 6.2% | 6.3% | 16.1% |
| 200ms | 6.6% | 3.8% | 5.5% | 4.3% | 2.6% | 3.4% | 3.6% | 8.1% |
| 300ms | 5.8% | 3.9% | 6.0% | 3.6% | 2.7% | 3.8% | 4.0% | 9.4% |
| 400ms | 4.8% | 3.7% | 4.1% | 3.3% | 2.8% | 2.9% | 3.1% | 5.8% |
| 500ms | 3.9% | 3.2% | 3.9% | 2.6% | 2.4% | 2.4% | 3.1% | 5.2% |
| 600ms | 3.9% | 2.5% | 3.7% | 2.6% | 1.8% | 2.3% | 2.8% | 4.3% |
| 700ms | 2.7% | 2.3% | 3.7% | 1.7% | 1.6% | 2.4% | 2.2% | 4.3% |
| 800ms | 3.5% | 1.8% | 2.9% | 2.3% | 1.6% | 1.8% | 2.1% | 4.5% |
| 900ms | 3.7% | 2.1% | 3.3% | 2.3% | 1.5% | 2.0% | 2.3% | 5.4% |
| 1000ms | 3.3% | 1.4% | 2.4% | 2.0% | 1.1% | 1.5% | 1.7% | 3.1% |
| 2000ms | 2.1% | 1.1% | 1.6% | 1.1% | 1.0% | 1.1% | 1.3% | 1.6% |
| 3000ms | 1.2% | 0.8% | 1.3% | 0.6% | 0.9% | 0.9% | 0.8% | 1.3% |
| 4000ms | 1.1% | 0.8% | 1.2% | 0.6% | 1.1% | 1.2% | 0.9% | 1.4% |
| 5000ms | 1.1% | 0.7% | 1.0% | 1.1% | 0.9% | 1.2% | 0.7% | 0.9% |

Fig.8

| VARIATION COEFFICIENT | ABSORPTION COEFFICIENT [1/cm] | | | SCATTERING COEFFICIENT [1/cm] | | | AMOUNT OF HEMOGLOBIN | |
|---|---|---|---|---|---|---|---|---|
| | 760nm | 800nm | 830nm | 760nm | 800nm | 830nm | tHb [μM] | SO2 [%] |
| 100ms | 5.2% | 5.0% | 4.7% | 2.4% | 2.4% | 2.4% | 4.9% | 4.3% |
| 200ms | 3.7% | 3.3% | 3.0% | 2.0% | 2.0% | 2.0% | 3.2% | 2.4% |
| 300ms | 3.6% | 3.1% | 3.4% | 2.1% | 2.1% | 2.1% | 3.6% | 1.9% |
| 400ms | 3.2% | 2.8% | 2.9% | 2.1% | 2.1% | 2.1% | 3.2% | 1.5% |
| 500ms | 3.4% | 2.3% | 2.8% | 1.8% | 1.8% | 1.8% | 2.8% | 1.3% |
| 600ms | 2.8% | 1.9% | 2.2% | 1.5% | 1.5% | 1.5% | 2.4% | 1.2% |
| 700ms | 2.3% | 1.4% | 1.8% | 1.0% | 1.0% | 1.0% | 1.9% | 1.2% |
| 800ms | 1.9% | 1.2% | 1.9% | 1.2% | 1.2% | 1.2% | 1.8% | 0.9% |
| 900ms | 2.2% | 1.5% | 1.8% | 0.9% | 0.9% | 0.9% | 1.9% | 0.9% |
| 1000ms | 1.9% | 1.3% | 1.7% | 0.9% | 0.9% | 0.9% | 1.7% | 0.7% |
| 2000ms | 0.8% | 0.6% | 0.8% | 0.6% | 0.6% | 0.6% | 0.8% | 0.7% |
| 3000ms | 0.8% | 0.6% | 0.8% | 0.6% | 0.6% | 0.6% | 0.8% | 0.5% |
| 4000ms | 0.9% | 0.4% | 0.8% | 0.8% | 0.8% | 0.8% | 0.7% | 0.5% |
| 5000ms | 0.7% | 0.5% | 0.8% | 0.9% | 0.9% | 0.9% | 0.7% | 0.6% |

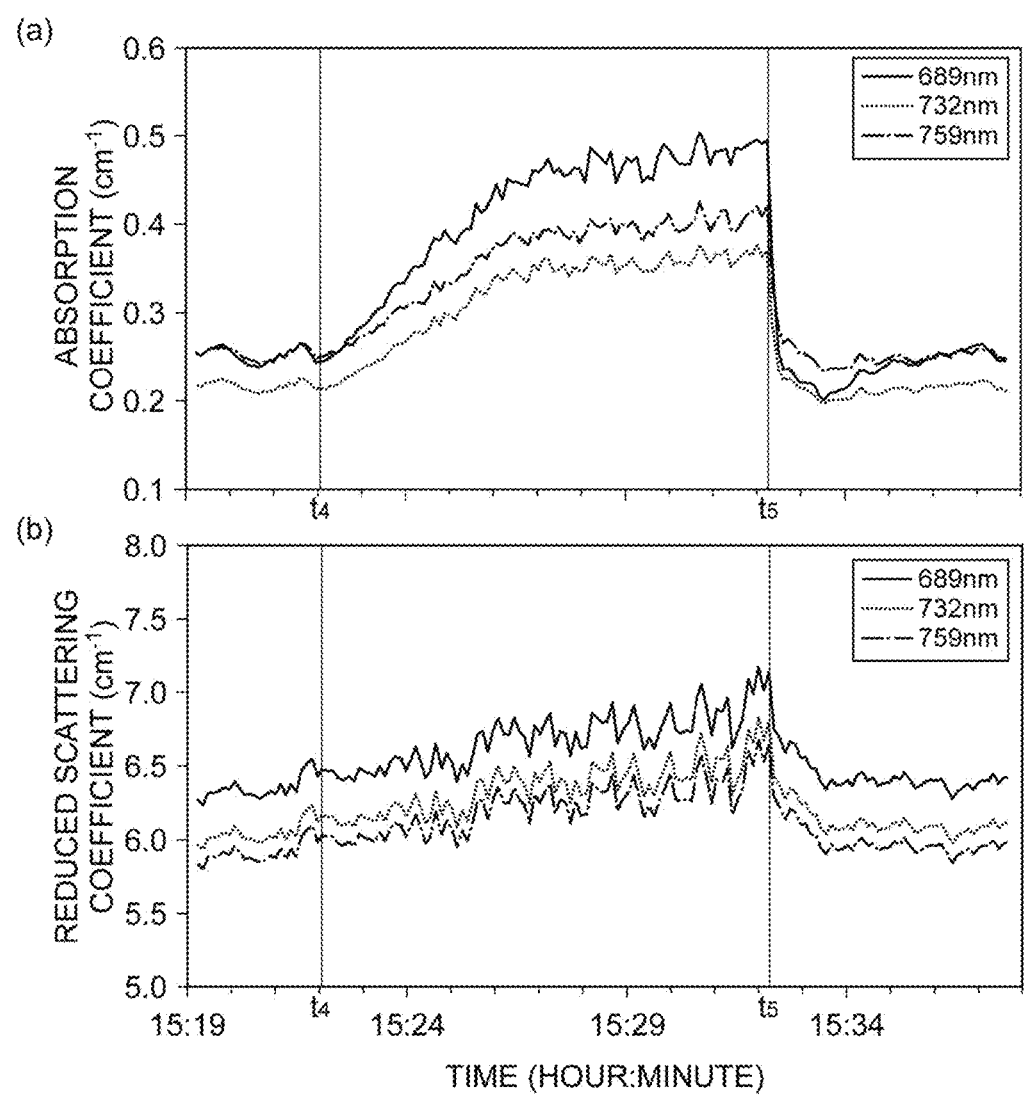

SCATTERING ABSORBER MEASUREMENT DEVICE AND SCATTERING ABSORBER MEASUREMENT METHOD

TECHNICAL FIELD

An aspect of the present invention relates to a scattering absorber measurement device and a scattering absorber measurement method.

BACKGROUND ART

Patent Literature 1 describes a method and device for measuring internal information of a scattering absorber. In the method and device described in this literature, light pulses of a plurality of wavelengths are incident on the scattering absorber, output light is detected by a photodetector, and the internal information of the scattering absorber is calculated on the basis of a detection result. When internal information is calculated, the internal information of the scattering absorber is calculated by calculating an absorption coefficient difference with a time-resolved integration measurement method (a TIS method) and a phase modulation measurement method (a PMS method) based on an MBL law according to a spectroscopic measurement method (an MVS method) using an optical path length average and variance or physical amounts corresponding thereto.

Non-Patent Literature 1 describes a method of measuring the concentrations of oxygenated hemoglobin and deoxygenated hemoglobin by using near infrared time-resolved spectroscopy. In the method described in this literature, a reduced scattering coefficient is set as a function of a wavelength by applying Mie scattering approximation and the concentration is calculated on the basis of each wavelength value.

CITATION LIST

Patent Literature

[Patent Literature 1] Japanese Unexamined Patent Publication No. 2000-146828

Non Patent Literature

[Non-Patent Literature 1] C. D' Andrea et al., "Time-resolved spectrally constrained method for the quantification of chromophore concentrations and scattering parameters in diffusing media", OPTICS EXPRESS, Vol. 14, No. 5, pp. 1888-1898, 6 Mar. 2006

[Non-Patent Literature 2] M. S. Patterson et. al., "Time resolved reflectance and transmittance for non-invasive measurement of tissue", Optical Properties, Appl Optics 28, pp. 2331-2336, 1989

SUMMARY OF INVENTION

Technical Problem

When the internal information of the scattering absorber is noninvasively measured using light, the internal information may be calculated using reduced scattering coefficients in a plurality of wavelengths. For example, when concentration information of the light absorbing material is calculated as the internal information, the absorption coefficient and the reduced scattering coefficient in each wavelength are calculated, and the concentration information is calculated on the basis of these values. In such a case, according to the conventional general method, the internal information is calculated after the reduced scattering coefficient and the absorption coefficient are calculated for each wavelength using a photon diffusion theory on the basis of detection results for each wavelength.

However, in the above-described method, for example, if an S/N ratio of the detection signal decreases when a distance between an incident position and a detection position of the light is long or the light absorbing material concentration is significantly increased, there is a problem in that the accuracy of the reduced scattering coefficient is significantly affected and consequently the accuracy of calculation of the internal information is lowered. Although a technique in which the wavelength dependence of the reduced scattering coefficient is considered is proposed in Non-Patent Literature 1, the Mie scattering approximation is used for the wavelength dependence of the reduced scattering coefficient. Because a uniform sphere of any material in a homogeneous medium (a diameter approximately equal to the wavelength) is assumed in the theory of Mie scattering, for example, an error increases in an actual scattering absorber such as living body tissue.

An aspect of the present invention has been made in view of such a problem and an objective of the aspect of the present invention is to provide a device and method capable of accurately calculating a reduced scattering coefficient and an absorption coefficient.

Solution to Problem

According to an aspect of the present invention for solving the above-described problem, a scattering absorber measurement device is a device for measuring a reduced scattering coefficient and an absorption coefficient of a scattering absorber, the device including: a light source for outputting a plurality of light pulses having different wavelengths input to a scattering absorber, a photodetector for detecting each light pulse propagating inside the scattering absorber and output a detection signal; and a computation unit for calculating a reduced scattering coefficient and an absorption coefficient according to a time-resolved spectroscopic measurement method on the basis of the detection signal, wherein the computation unit determines data related to a ratio of reduced scattering coefficients among wavelengths of the plurality of light pulses and calculates the reduced scattering coefficient and the absorption coefficient on the basis of a time-resolved measurement profile of each wavelength based on the detection signal and the data.

Also, a scattering absorber measurement method according to an aspect of the present invention is a method of measuring a reduced scattering coefficient and an absorption coefficient, the method including the steps of: inputting a plurality of light pulses having different wavelengths to a scattering absorber (an inputting step); detecting each light pulse propagating inside the scattering absorber and outputting a detection signal (a light detecting step); and calculating the reduced scattering coefficient and the absorption coefficient according to a time-resolved spectroscopic measurement method on the basis of the detection signal (a calculating step), wherein data related to a ratio of reduced scattering coefficients among wavelengths of the plurality of light pulses is determined and the reduced scattering coefficient and the absorption coefficient are calculated on the basis of a time-resolved measurement profile of each wavelength based on the detection signal and the data in the calculating step.

In the above-described scattering absorber measurement device and scattering absorber measurement method, the data related to the ratio of the reduced scattering coefficients among the plurality of light pulses is determined. Because the reduced scattering coefficient has a predetermined correlation with the wavelength, the ratio of the reduced scattering coefficients among the wavelengths is regarded to be substantially constant through a plurality of measurements. In the computation unit (the calculating step), the reduced scattering coefficient of each wavelength conforms to the ratio of the reduced scattering coefficients and the reduced scattering coefficient and the absorption coefficient are calculated on the basis of the time-resolved measurement profile of each wavelength based on the detection signal and the determined data. According to this scheme, it is possible to further improve the accuracy of calculation of the reduced scattering coefficient and the absorption coefficient than in a method of applying a photon diffusion theory to the time-resolved measurement profile of each wavelength and calculating the reduced scattering coefficient and the absorption coefficient.

In the above-described scattering absorber measurement device, the computation unit may perform fitting based on a light diffusion equation with respect to the time-resolved measurement profile of each wavelength, while associating the reduced scattering coefficient in each wavelength on the basis of the determined data. Likewise, in the above-described scattering absorber measurement method, fitting based on a light diffusion equation may be performed with respect to the time-resolved measurement profile of each wavelength, while associating the reduced scattering coefficient in each wavelength on the basis of the determined data in the calculating step. According to this scheme, it is possible to improve the accuracy of calculation of the reduced scattering coefficient and the absorption coefficient because fitting is performed with respect to a plurality of time-resolved measurement profiles, while associating the reduced scattering coefficient in each wavelength.

Also, in the above-described scattering absorber measurement device, the computation unit may perform weighting based on the time-resolved measurement profile of each wavelength with respect to the reduced scattering coefficient of each wavelength used in the fitting. Likewise, in the above-described scattering absorber measurement method, weighting based on the time-resolved measurement profile of each wavelength may be performed with respect to the reduced scattering coefficient of each wavelength used in the fitting in the calculating step. When the light pulse is detected in the photodetector (the light detecting step), variation in reliability of a detection result between wavelengths may occur according to the number of detected photons, the S/N ratio, or the like. In this case, weighting is performed in consideration of the time-resolved measurement profile and therefore it is possible to further improve the accuracy of calculation of the reduced scattering coefficient and the absorption coefficient.

In the above-described scattering absorber measurement device and scattering absorber measurement method, the data related to the ratio of the reduced scattering coefficients among the wavelengths of the plurality of light pulses may be stored in a storage device. According to this scheme, it is possible to further improve the accuracy of calculation of the reduced scattering coefficient and the absorption coefficient because data related to a ratio of reduced scattering coefficients can be accurately measured under favorable conditions in advance.

Advantageous Effects of Invention

According to the scattering absorber measurement device and the scattering absorber measurement method based on the aspects of the present invention, it is possible to accurately calculate a reduced scattering coefficient and an absorption coefficient.

BRIEF DESCRIPTION OF DRAWINGS

FIG. 5 is a table illustrating a reduced scattering coefficient obtained by measuring a human forehead which is a scattering absorber using a reduced scattering coefficient ratio $R_1:R_2:R_3=1.0366:1.0000:0.9595$ confirmed in a wavelength $\lambda_1=759$ nm, a wavelength $\lambda_2=793$ nm, and a wavelength $\lambda_3=834$ nm in the wavelength dependency of the reduced scattering coefficient illustrated in FIG. 3.

FIGS. 6(a) and 6(b) are tables illustrating an absorption coefficient and a reduced scattering coefficient of each wavelength and an absorption coefficient and a reduced scattering coefficient of each wavelength as a comparative example measured according to a conventional method.

FIG. 6(c) is a table illustrating an oxygenated hemoglobin concentration, a deoxygenated hemoglobin concentration, a total hemoglobin concentration, and a degree of tissue oxygen saturation.

FIG. 7 is a table illustrating change coefficient values of an absorption coefficient, a reduced scattering coefficient, and a hemoglobin amount obtained by changing a measurement time when a forehead portion is measured.

FIG. 8 is a table illustrating change coefficient values of an absorption coefficient, a reduced scattering coefficient, and a hemoglobin amount obtained by changing a measurement time when a forehead portion is measured.

FIG. 12 is a graph illustrating results of measuring an absorption coefficient and a reduced scattering coefficient of each wavelength of a human forearm portion.

DESCRIPTION OF EMBODIMENTS

Hereinafter, embodiments of a scattering absorber measurement device and a scattering absorber measurement method according to aspects of the present invention will be described in detail with reference to the accompanying drawings. The same reference signs are assigned to the same elements in the description of the drawings and redundant description thereof will be omitted.

(Embodiments)

Figure 1:
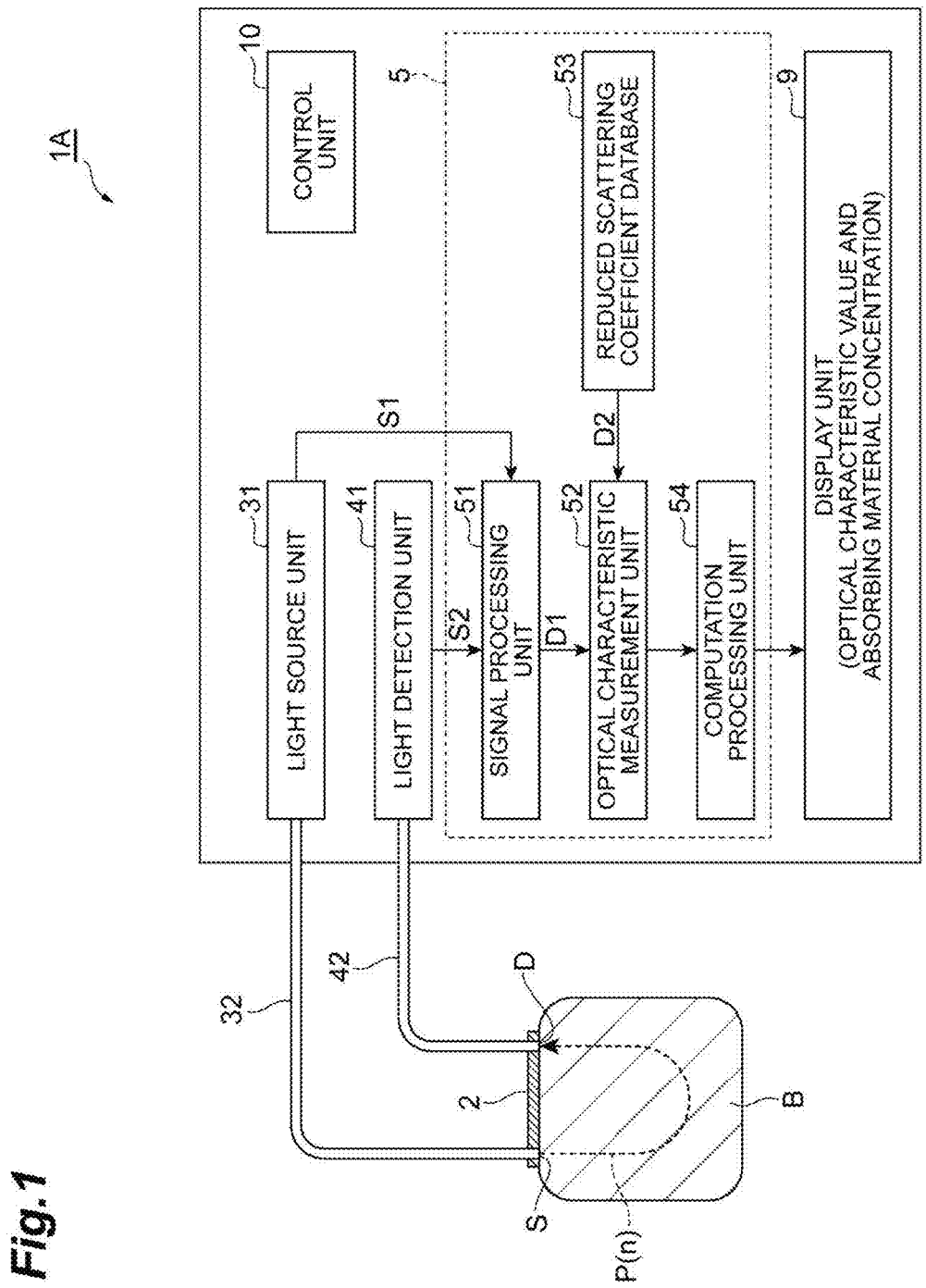
FIG. 1 is a block diagram schematically illustrating a configuration of an embodiment of a measurement device according to an aspect of the present invention.

FIG. 1 is a block diagram schematically illustrating a configuration of a first embodiment of a measurement device according to an aspect of the present invention. This measurement device 1A is a device that measures internal information of a scattering absorber B by a time-resolved spectroscopic measurement method using near-infrared light. The scattering absorber B is, for example, a part of a living body, and the internal information is, for example, an oxygenated hemoglobin concentration, a deoxygenated hemoglobin concentration, a total hemoglobin concentration, a degree of oxygen saturation, and the like. Because it is possible to quantitatively measure a hemoglobin dynamic state noninvasively and simply, the measurement device 1A can be applied to cerebral oxygen metabolism monitoring during surgery, muscle evaluation during exercise, and the like.

As illustrated in FIG. 1, the measurement device 1A includes a light source unit 31, a light irradiation fiber 32, a light detection unit 41, a light detection fiber 42, a computation unit 5, a display unit 9, and a control unit 10 that controls these components.

The light source unit 31 and the light irradiation fiber 32 are light input units in the present embodiment, and input a plurality of lights having different wavelengths to the scattering absorber B. The light source unit 31 is a light source that outputs light input to the scattering absorber B. For example, the light source unit 31 generates N (N is an integer equal to or greater than 2) light pulses P(1) to P(N). Center wavelengths of the N light pulses P(1) to P(N) are different from each other, and a full width at half maximum of each light pulse P(n) (where n=1, . . . , N) is, for example, 10 ps to several ns. One end of the light irradiation fiber 32 is optically connected to the light source unit 31 and the other end (a light input end) of the light irradiation fiber 32 is arranged at a predetermined light input position S on a surface of the scattering absorber B. Each light pulse P(n) output from the light source unit 31 is input to one end of the light irradiation fiber 32 and radiated from the other end of the light irradiation fiber 32 to the inside of the scattering absorber B. The light source unit 31 is electrically connected to a signal processing unit 51 of the computation unit 5 (to be described below), and outputs a trigger signal S1 indicating light emission timings of the light pulses P(1) to P(N) in the light source unit 31 to the signal processing unit 51. Also, the light emission timings of the light pulses P(1) to P(N) are controlled by the control unit 10.

As the light source unit 31, various types such as a light emitting diode, a laser diode, a super luminescent diode, and various pulse laser devices are used. As the light pulse P(n) generated in the light source unit 31, a near infrared light pulse in which a time width of the pulse is short enough to measure an amount of change in the absorption coefficient of the scattering absorber B and a wavelength having a low light absorption rate is a center wavelength in light absorption characteristics of a material to be measured is used. In an example, n=3, and the wavelengths of the light pulses P(1) to P(3) are 760 nm, 800 nm, and 830 nm, respectively.

The light detection unit 41 and the light detection fiber 42 detect light propagating inside the scattering absorber B. The light detection unit 41 is a photodetector that detects each light pulse propagating inside the scattering absorber B and outputs a detection signal. One end (a light detection end) of the light detection fiber 42 is arranged at a predetermined light detection position D on the surface of the scattering absorber B and the other end of the light detection fiber 42 is optically connected to the light detection unit 41. The light detection unit 41 detects light to be detected generated when the light pulse P(n) propagates inside the scattering absorber B via the light detection fiber 42. A signal output terminal of the light detection unit 41 is electrically connected to the signal processing unit 51 of the computation unit 5 (to be described below), and the light detection unit 41 outputs a light detection signal (a detection signal) S2 indicating a detection timing of the detected light (photons) to the signal processing unit 51. Because this light detection signal S2 indicates a detection timing when one photon is detected, it is possible to obtain a time-resolved measurement profile which is a change over time in the intensity of the detected light when the number of photons detected at each detection timing is plotted.

Various photodetectors such as a photomultiplier tube (PMT), an avalanche photodiode, a PIN photodiode, and a multi-pixel photon counter (MPPC) are used as the light detection unit 41. Also, it is preferable that the light detection unit 41 have a spectral sensitivity characteristic capable of sufficiently detecting each of wavelengths of the light pulses P(1) to P(N). Also, when the detected light is weak, a photodetector with high sensitivity or high gain may be used. Further, the light detection unit 41 is not limited to outputting the light detection signal S2 indicating the detection timing of the detected light, and may output the light detection signal S2 indicating the intensity of the detected light.

In one example, the light input end of the light irradiation fiber 32 and the light detection end of the light detection fiber 42 are fixed to the optical fiber holder 2 arranged on the surface of the scattering absorber B. The optical fiber holder 2 is, for example, a pad. Preferably, for example, the optical fiber holder 2 may be constituted of a member that is flexible and deformable along the surface of the scattering absorber B.

Also, the optical fiber holder 2 can also be omitted. Further, instead of using the light irradiation fiber 32 and the light detection fiber 42, the light source unit 31 and the light detection unit 41 may be provided in the optical fiber holder 2. In this case, the light pulse P(n) output from the light source unit 31 is directly input to the scattering absorber B. Also, in this case, the light detection unit 41 detects light to be detected output from the scattering absorber B on the surface of the scattering absorber B.

Figure 2:
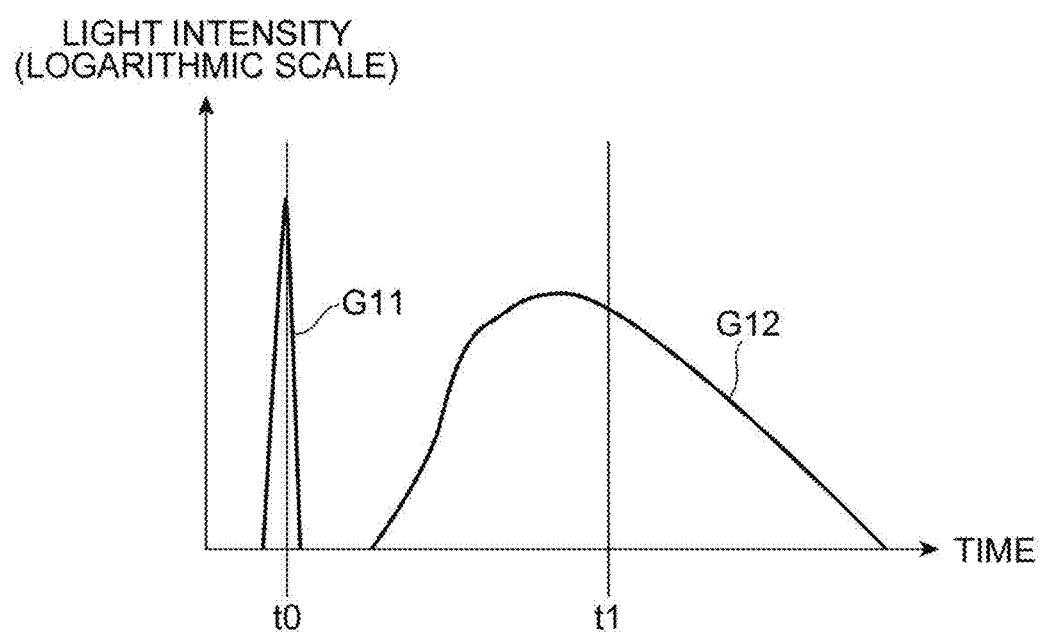
FIG. 2 is a graph illustrating an example of changes over time in light intensities of a light pulse output from a light source unit and light to be detected which is detected in a light detection unit.

FIG. 2 is a graph illustrating an example of a time-resolved measurement profile which is a change over time in the light intensity of the light to be detected, detected by the light detection unit 41 when the light pulse P(n) output from the light source unit 31 is input to the scattering absorber B. In FIG. 2, the vertical axis represents light intensity (logarithmic scale) and the horizontal axis represents time. Graph G11 is a time waveform (an input waveform) of the light pulse intensity input from the light source unit 31 to the scattering absorber B at time $t_0$. Graph G12 is a time waveform (a detection waveform) of the detected light intensity corresponding to the light pulse input at time $t_0$. A time at which the light propagating inside the scattering absorber B reaches the light detection position D is not uniform according to a propagation state and the light is attenuated by scattering and absorption in the scattering absorber B. Accordingly, as illustrated in the graph G12 of FIG. 2, the detection waveform has a certain fixed distribution curve.

FIG. 1 is referred to again. The computation unit 5 calculates the reduced scattering coefficient and the absorption coefficient inside the scattering absorber B on the basis of the detection result of the light detection unit 41, and further calculates the internal information. The computation unit 5 is, for example, a computer. The computation unit 5 has a processor, and the processor operates as a signal processing unit 51, an optical characteristic measurement unit 52, and a computation processing unit 54 according to a computation program. Accordingly, the computation unit 5 includes the signal processing unit 51, the optical characteristic measurement unit 52, a reduced scattering coefficient database 53, and the computation processing unit 54.

The signal processing unit 51 is electrically connected to the light source unit 31 and receives a trigger signal S1 indicating the light emission timing of the light pulses P(1) to P(N) in the light source unit 31. Also, the signal processing unit 51 is electrically connected to the light detection unit 41, and receives a light detection signal S2 indicating a detection timing of the detected light (photons). On the basis of the trigger signal S1 and light detection signal S2, the signal processing unit 51 acquires a plurality of (N) time-resolved measurement waveforms (a time-resolved measurement profile) by a time-correlated single photon counting method. The signal processing unit 51 outputs data D1 related to the N time-resolved measurement waveforms obtained thereby to the optical characteristic measurement unit 52.

The optical characteristic measurement unit 52 calculates the reduced scattering coefficient and the absorption coefficient on the basis of the data D1 related to the time-resolved measurement waveform of each wavelength acquired on the basis of the light detection signal S2 and data D2 related to a ratio of reduced scattering coefficients among wavelengths of a plurality of light pulses. In detail, the optical characteristic measurement unit 52 uses the data D1 related to the N time-resolved measurement waveforms provided from the signal processing unit 51 and calculates the absorption coefficient and the reduced scattering coefficient on the basis of a light diffusion equation (a photon diffusion theory). The optical characteristic measurement unit 52 of the present embodiment reads the data D2 previously stored in the reduced scattering coefficient database 53, and calculates a reduced scattering coefficient by using the data D2. The reduced scattering coefficient database 53 is a storage device (storage) for storing data related to the ratio of reduced scattering coefficients among the wavelengths of a plurality of light pulses. For example, the reduced scattering coefficient database 53 is stored in an auxiliary storage device of a computer or an external storage device electrically connected to the computer. The data D2 includes information about a ratio $R_1:R_2: \ldots :R_N$ of the reduced scattering coefficients among wavelengths $\lambda_1, \lambda_2, \ldots, \lambda_N$ of the plurality of light pulses P(1) to P(N). This information is a numerical value obtained by previously measuring a reduced scattering coefficient for each wavelength of a basic scattering absorber under suitable conditions before the measurement device 1A is used (for example, when the measurement device 1A is manufactured).

Figure 3:
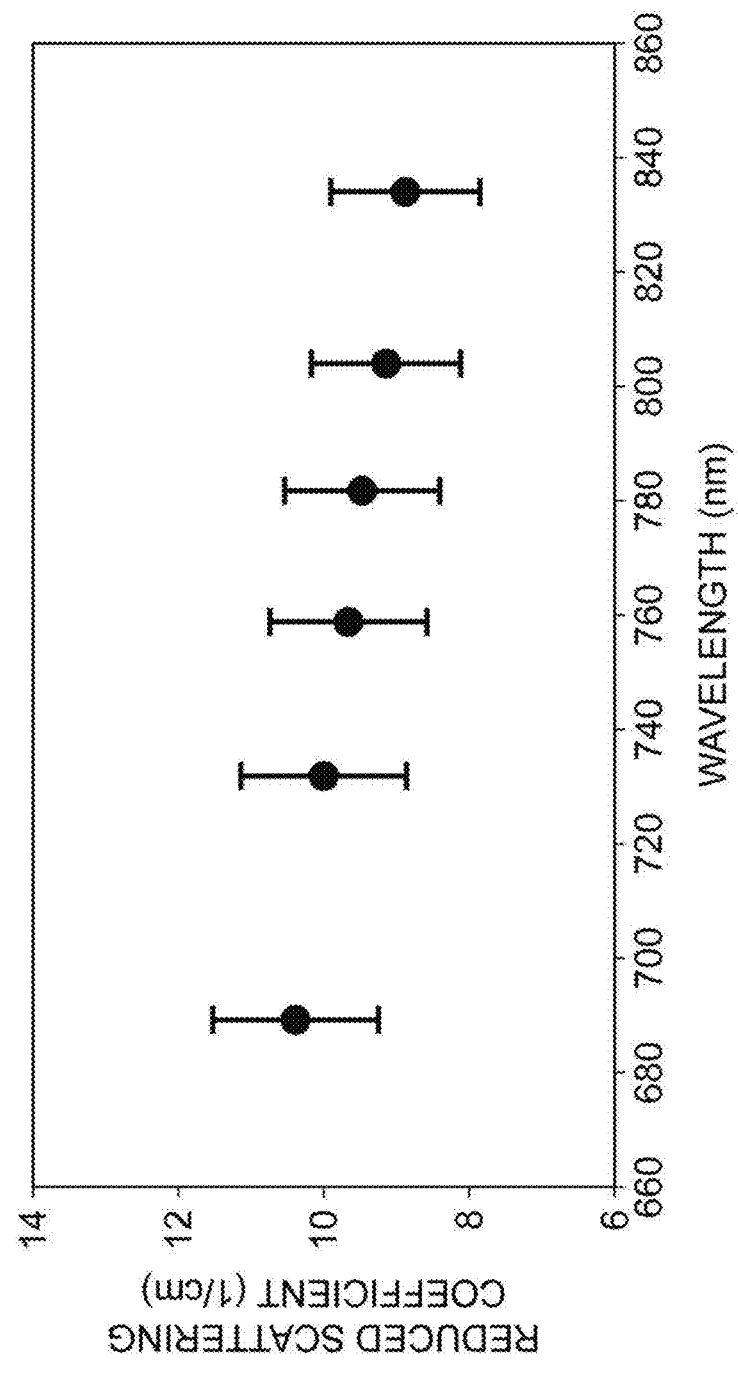
FIG. 3 is a graph illustrating a relationship between a reduced scattering coefficient and a wavelength.

Here, FIG. 3 is a graph illustrating a relationship between a reduced scattering coefficient and a wavelength obtained by the present inventor measuring reduced scattering coefficients with respect to left and right forehead portions of 50 adult males and females. In FIG. 3, a standard deviation (a mark I in FIG. 3) and an average value (a black circle in FIG. 3) of the reduced scattering coefficient measured in each of six wavelengths included within a wavelength range from 690 nm to 840 nm are illustrated. As illustrated in FIG. 3, there is a significant correlation between the reduced scattering coefficient and the wavelength. Generally, as the wavelength increases, the reduced scattering coefficient decreases. Also, it can be seen that the reduced scattering coefficients conform to a fixed ratio between the wavelengths.

It is assumed that the optical characteristic measurement unit 52 reads the data D2 from the reduced scattering coefficient database 53 and the reduced scattering coefficient of each wavelength conforms to the ratio $R_1:R_2: \ldots :R_N$. In other words, the optical characteristic measurement unit 52 assumes reduced scattering coefficients for wavelengths as $R_1 \cdot \mu'_{s,R}, R_2 \cdot \mu'_{s,R}, \ldots, R_N \cdot \mu'_{s,R}$ (where $\mu'_{s,R}$ is a basic reduced scattering coefficient). Then, the optical characteristic measurement unit 52 collectively fits time-resolved measurement profiles in the plurality of wavelengths $\lambda_1, \lambda_2, \ldots, \lambda_N$ based on the data D1 to a solution of the light diffusion equation to calculate the basic reduced scattering coefficient $\mu'_{s,R}$ and the absorption coefficient $\mu_{a,\lambda}$ ($\lambda=\lambda_1, \ldots, \lambda_N$) for each wavelength. Accordingly, the optical characteristic measurement unit 52 performs fitting on the time-resolved measurement profile of each wavelength based on the light diffusion equation, while associating the reduced scattering coefficients in wavelengths on the basis of the data D2. It is possible to calculate the reduced scattering coefficient for each wavelength when the basic reduced scattering coefficient $\mu'_{s,R}$ is multiplied by each ratio $R_1:R_2: \ldots :R_N$. Also, the basic reduced scattering coefficient $\mu'_{s,R}$ is a reduced scattering coefficient in a basic wavelength. For example, the basic wavelength in FIG. 5 is 793 nm, and the basic reduced scattering coefficient $\mu'_{s,R}$ is 10.287.

Preferably, as a more preferable form, the optical characteristic measurement unit 52 may further perform weighting based on the time-resolved measurement profile in each wavelength on the reduced scattering coefficient for each wavelength. Preferably, as an example, the optical characteristic measurement unit 52 determines measurement reliability of each wavelength from an S/N ratio of N time-resolved measurement waveforms included in the data D1 and/or intensities (the number of detected photons) of detected light corresponding to the light pulses P(1) to P(N) and weight distribution calculated from the measurement reliability may be given when the reduced scattering coefficient for each wavelength is applied to the light diffusion equation.

As a solution to the light diffusion equation used for fitting, there is, for example, a solution disclosed in the above-mentioned Non-Patent Literature 2. As an example, if scattering coefficients $R_1 \cdot \mu'_{s,R}, R_2 \cdot \mu'_{s,R}, \ldots, R_N \cdot \mu'_{s,R}$ are applied to a solution of reflection type measurement (boundary condition: zero boundary condition) in semi-infinite slab, the following Equations (1) are obtained for each wavelength. Here, $F_1(\rho, t), \ldots, F_N(\rho, t)$ are reflection type time response functions in wavelengths $\lambda_1, \ldots, \lambda_n$. Also, $\rho$ is a distance between optical axes, t is a response time, and c is a speed of light in the scattering absorber.

[Math. 1]

$$F_1(\rho, t) = \qquad (1)$$
$$\left(\frac{4\pi c}{3}\right)^{-3/2}(R_1\mu'_{s,R})^{1/2}t^{-5/2}\exp(-\mu_{a,\lambda_1}ct)\exp\left(-\frac{3\left(R_1\mu'_{s,R}\rho^2+\frac{1}{R_1\mu'_{s,R}}\right)}{4ct}\right),$$
$$\vdots$$
$$F_N(\rho, t) =$$
$$\left(\frac{4\pi c}{3}\right)^{-3/2}(R_N\mu'_{s,R})^{1/2}t^{-5/2}\exp(-\mu_{a,\lambda_N}ct)\exp\left(-\frac{3\left(R_N\mu'_{s,R}\rho^2+\frac{1}{R_N\mu'_{s,R}}\right)}{4ct}\right)$$

Also, although the reduced scattering coefficient ratio $R_1:R_2:\ldots:R_N$ is pre-stored in the reduced scattering coefficient database 53 in this embodiment, the optical characteristic measurement unit 52 may determine the data D2 by inputting the reduced scattering coefficient ratio $R_1:R_2:\ldots:R_N$ from the outside of the measurement device 1A via an input device (not illustrated). Also, for example, the reduced scattering coefficient ratio $R_1:R_2:\ldots:R_N$ is preferably constructed as a database according to use of MRI or ultrasonic data capable of measuring the structure and moisture content in the scattering absorber B (for example, living body tissue) and collection of reduced scattering coefficient data for each of various measurement sites, inter-fiber distances, ages and genders in the time-resolved spectroscopic device in a state in which sufficient accuracy of measurement is implemented.

Also, at the time of fitting, the absorption coefficient and the basic reduced scattering coefficient $\mu'_{s,R}$ of each wavelength are determined using a nonlinear least squares method based on a Levenberg-Marquardt method so that the difference between the N time-resolved measurement waveforms and the above Equations (1) approach the minimum. Thereafter, the optical characteristic measurement unit 52 outputs the determined basic reduced scattering coefficient $\mu'_{s,R}$ or the reduced scattering coefficients $R_1\cdot\mu'_{s,R}$, $R_2\cdot\mu'_{s,R}$, ..., $R_N\cdot\mu'_{s,R}$ of wavelengths, and the absorption coefficients $\mu_{a,\lambda}$ (=$\lambda_1$, ..., $\lambda_N$) of the wavelengths to the computation processing unit 54.

The computation processing unit 54 calculates internal information inside the scattering absorber B, for example, an absorbing material concentration. As an example, the computation processing unit 54 of the present embodiment calculates an oxygenated hemoglobin concentration $C_{HbO2}$ and a deoxygenated hemoglobin concentration $C_{Hb}$ by applying the absorption coefficients $\mu_{a,\lambda}$ ($\lambda=\lambda_1, \ldots, \lambda_N$) of wavelengths provided from the optical characteristic measurement unit 52 to the following Equation (2) and solving N simultaneous equations. Also, $\varepsilon_{HbO2,\lambda}$ is a molar absorption coefficient of oxygenated hemoglobin in the wavelength $\lambda$, and $\varepsilon_{Hb,\lambda}$ is a molar absorption coefficient of deoxygenated hemoglobin in the wavelength $\lambda$.

[Math. 2]

$$\mu_{a,\lambda}=\varepsilon_{HbO2,\lambda}C_{HbO2}+\varepsilon_{Hb,\lambda}C_{Hb} \qquad (2)$$

Further, the computation unit 54 may calculate a degree of tissue oxygen saturation $SO_2$ from the following Equation (3) on the basis of the calculated oxygenated hemoglobin concentration $C_{HbO2}$ and deoxygenated hemoglobin concentration $C_{Hb}$.

[Math. 3]

$$SO_2 = \frac{C_{HbO2}}{C_{HbO2}+C_{Hb}} \qquad (3)$$

Any parameter (for example, the oxygenated hemoglobin concentration $C_{HbO2}$ or the deoxygenated hemoglobin concentration $C_{Hb}$) among the parameters calculated by the optical characteristic measurement unit 52 and the computation processing unit 54 is displayed on the display unit 9. A measurer and a test subject recognize a parameter value through this display unit 9.

Figure 4:
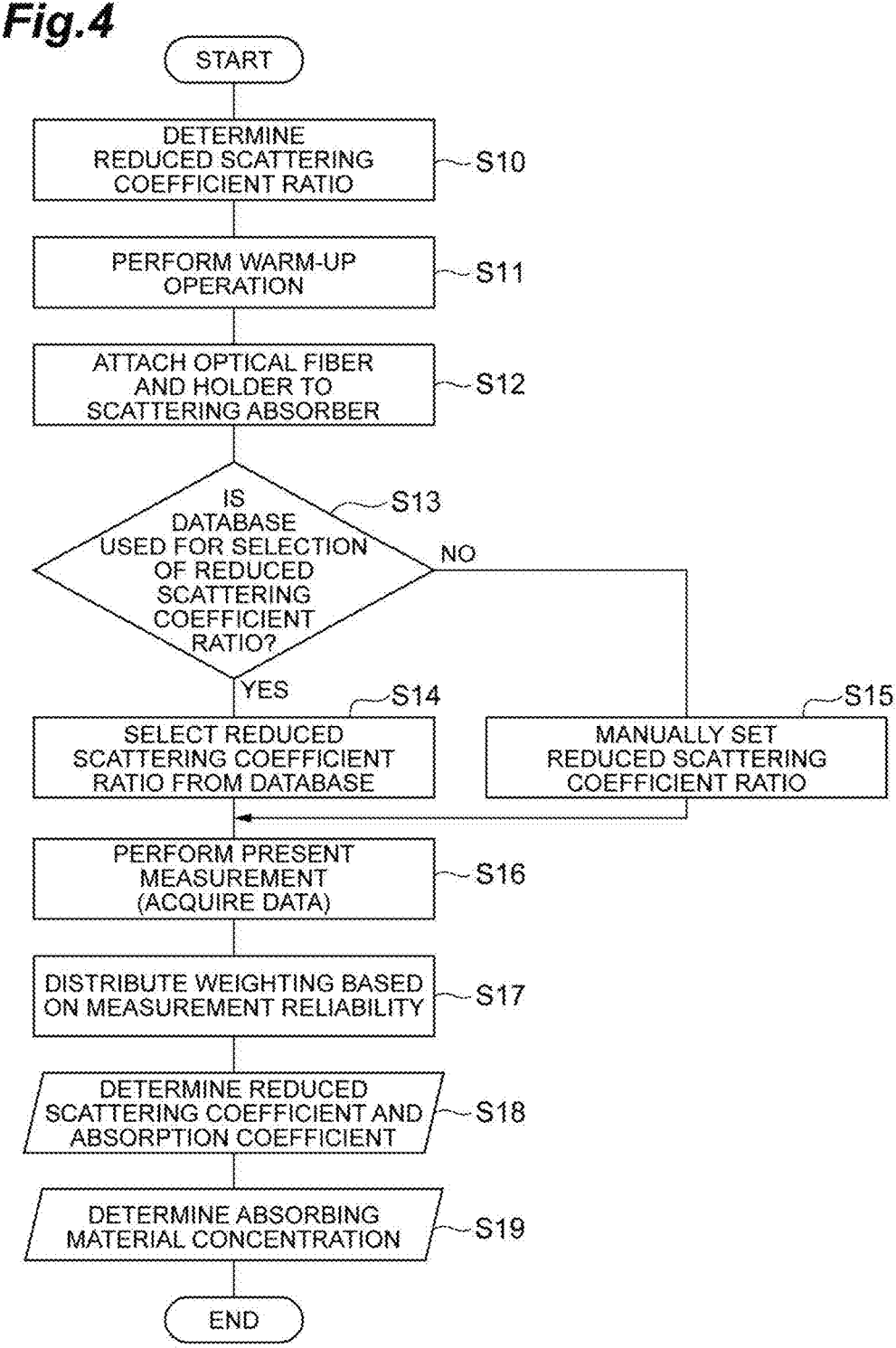
FIG. 4 is a flowchart illustrating an operation of the measurement device and a scattering absorber measurement method.

An operation of the measurement device 1A having the above configuration will be described together with the measurement method of the scattering absorber according to the present embodiment. FIG. 4 is a flowchart illustrating the operation of the measurement device 1A and the scattering absorber measurement method.

As illustrated in FIG. 4, the reduced scattering coefficient ratio $R_1:R_2:\ldots:R_N$ is determined by first measuring a plurality of scattering absorbers B (for example, living body tissues) under a stable condition that a high S/N ratio can be obtained (step S10). Preferably, at this time, for example, MRI or ultrasound data may be used to accurately measure the reduced scattering coefficient ratio. Preferably, because the reduced scattering coefficient significantly depends on the structure and moisture content in the scattering absorber, reduced scattering coefficient data according to ages, genders, measurement sites, distances between light input positions S and light detection positions D, and the like with respect to various test subjects may be collected using the time-resolved spectroscopic measurement method and a plurality of sets of reduced scattering coefficient ratios may be determined in advance. The determined reduced scattering coefficient ratio $R_1:R_2:\ldots:R_N$ may be stored in the reduced scattering coefficient database 53 or may be manually set at the time of measurement to be described below.

Next, the measurement device 1A is warmed up (step S11), and the optical fiber holder 2 to which the light irradiation fiber 32 and the light detection fiber 42 are attached is arranged on the surface of the scattering absorber B to be measured (step S12).

Then, a reduced scattering coefficient ratio suitable for the measurement object is selected from among the plurality of sets of reduced scattering coefficient ratios. At this time, it is determined whether or not to use the reduced scattering coefficient database 53 for selection of the reduced scattering coefficient ratio (step S13). If the reduced scattering coefficient database 53 is used (step S13; YES), the reduced scattering coefficient ratio suitable for a measurement object is selected from the reduced scattering coefficient database 53 (step S14). If the reduced scattering coefficient database 53 is not used (step S13; NO), the reduced scattering coefficient ratio suitable for the measurement object is manually set (step S15).

Subsequently, a plurality of light pulses P(n) having different wavelengths are sequentially input from the light source unit 31 to the light input position S of the scattering absorber B via the light irradiation fiber 32, and each light pulse P(n) propagating inside the scattering absorber B is guided to the light detection unit 41 via the light detection fiber 42 and detected (a light detecting step S16). Next, on the basis of the detection result in the light detection step S13, the signal processing unit 51 generates data D1 related to N time-resolved measurement waveforms. The data D1 is provided to the optical characteristic measurement unit 52.

Subsequently, the optical characteristic measurement unit 52 sets reduced scattering coefficients for wavelengths $\lambda_1, \ldots, \lambda_N$ to $R_1 \cdot \mu'_{s,R}, R_2 \cdot \mu'_{s,R}, \ldots, R_N \cdot \mu'_{s,R}$ which conform to a ratio $R_1:R_2:\ldots:R_N$ (where $\mu'_{s,R}$ is a basic scattering coefficient). At this time, the optical characteristic measurement unit 52 performs weighting based on reliability of detection results (N time-resolved measurement waveforms) for each wavelength with respect to the reduced scattering coefficient for each wavelength (step S17). As an example, preferably, the optical characteristic measurement unit 52 may determine measurement reliability of each wavelength from an S/N ratio of N time-resolved measurement waveforms included in the data D1 and/or intensities of detected light (the number of detected photons) corresponding to the light pulses P(1) to P(N) and give a weight distribution calculated from the measurement reliability.

Subsequently, the optical characteristic measurement unit 52 calculates the basic reduced scattering coefficients $\mu'_{s,R}$ and the absorption coefficients $\lambda_{a,\lambda}$ ($\lambda=\lambda_1, \ldots, \lambda_N$) for the wavelengths by the time-resolved spectroscopic measurement method (a calculating step S18). At this time, the optical characteristic measurement unit 52 calculates the basic reduced scattering coefficient $\mu'_{s,R}$ and the absorption coefficient $\lambda_{a,\lambda}$ ($\lambda=\lambda_1, \ldots, \lambda_N$) for each wavelength by collectively fitting time-resolved measurement profiles in the plurality of wavelengths based on the data D1 to a solution of the light diffusion equation.

Subsequently, the computation processing unit 54 calculates internal information inside the scattering absorber B, for example, the absorbing material concentration (step S19). As an example, the computation processing unit 54 of the present embodiment calculates the oxygenated hemoglobin concentration $C_{HbO2}$ and the deoxygenated hemoglobin concentration $C_{Hb}$ by applying the absorption coefficients $\mu_{a,\lambda}$ ($\lambda=\lambda_1, \ldots, \lambda_N$) of wavelengths provided from the optical characteristic measurement unit 52 to the following Equation (2) and solving N simultaneous equations. Also, a total hemoglobin concentration ($C_{tHb}=C_{HbO2}+C_{Hb}$), a degree of tissue oxygen saturation, and the like can also be calculated from these numerical values.

Advantageous effects obtained by the measurement device 1A and the measurement method of the above-described present embodiment will be described. As described above, in the present embodiment, data D2 related to the reduced scattering coefficient ratio $R_1:R_2:\ldots:R_N$ among wavelengths of a plurality of light pulses P(n) is provided in advance. Because the reduced scattering coefficient has a fixed correlation with the wavelength as illustrated in FIG. 3, a reduced scattering coefficient ratio $R_1:R_2:\ldots:R_N$ among a plurality of wavelengths is regarded to be substantially fixed through a plurality of measurements. Then, in the optical characteristic measurement unit 52 and the calculating step S18, reduced scattering coefficients of wavelengths are assumed to conform to the reduced scattering coefficient ratio $R_1:R_2:\ldots:R_N$ and the basic reduced scattering coefficient $\mu'_{s,R}$ and the absorption coefficient $\mu_{a,\lambda}$ ($\lambda=\lambda_1, \ldots, \lambda_N$) for each wavelength are calculated by collectively fitting time-resolved measurement profiles in the plurality of wavelengths based on the data D1 to a solution of the light diffusion equation. According to this scheme, it is possible to accurately measure data related to the reduced scattering coefficient ratio $R_1:R_2:\ldots:R_N$ in advance under favorable conditions and the accuracy of fitting also increases because a plurality of values are fitted simultaneously. Accordingly, it is possible to further improve the accuracy of calculation of the reduced scattering coefficient and the absorption coefficient than in a method of calculating the reduced scattering coefficient and the absorption coefficient by applying the photon diffusion theory for each wavelength.

Further, according to the measurement device 1A and the measurement method of the present embodiment, even when the accurate distance between the light input position S and the light detection position D is unknown, it is possible to accurately measure the absorption coefficient $\mu_{a,\lambda}$ ($\lambda=\lambda_1, \ldots, \lambda_N$) more than in the past by applying the reduced scattering coefficient ratio $R_1:R_2:\ldots:R_N$ and it is possible to further accurately measure an oxygenated hemoglobin concentration, a deoxygenated hemoglobin concentration, a total hemoglobin concentration, and a degree of tissue oxygen saturation.

Also, as in the present embodiment, the weighting based on the reliability of N time-resolved measured waveforms may be performed with respect to the reduced scattering coefficient for each wavelength used for fitting. When light is detected in the light detection unit 41 (a light detecting step S16), the reliability of N time-resolved measurement waveforms may vary with the number of detected photons, the S/N ratio, or the like. Even in such a case, by performing weighting in consideration of reliability, the influence of a wavelength with a low S/N ratio can be minimized, and the accuracy of calculation of the reduced scattering coefficient and the absorption coefficient can be further improved.

Here, results of measuring reduced scattering coefficients, oxygenated hemoglobin concentrations, deoxygenated hemoglobin concentrations, degrees of tissue oxygen saturation, and the like of a plurality of test subjects using the measurement device 1A and the measurement method of the present embodiment will be described.

FIG. 5 is a table illustrating a reduced scattering coefficient obtained by measuring a human forehead which is a scattering absorber using a reduced scattering coefficient ratio $R_1:R_2:R_3=1.0366:1.0000:0.9595$ confirmed in a wavelength $\lambda_1=759$ nm, a wavelength $\lambda_2=793$ nm, and a wavelength $\lambda_3=834$ nm in the wavelength dependency of the reduced scattering coefficient illustrated in FIG. 3. Also, in FIG. 5, numerical values obtained by a conventional measurement method (a reduced scattering coefficient is determined for each wavelength) are illustrated as a comparative example. Referring to FIG. 5, it can be seen that the reduced scattering coefficient ratio obtained according to the present embodiment conforms to the above-mentioned reduced scattering coefficient ratio $R_1:R_2:R_3$.

Also, FIGS. 6(a) and 6(b) are tables illustrating an absorption coefficient and a reduced scattering coefficient of each wavelength measured according to the measurement device 1A and the measurement method of the present embodiment and an absorption coefficient and a reduced scattering coefficient of each wavelength as a comparative example measured according to a conventional method. Further, FIG. 6(c) is a table illustrating an oxygenated hemoglobin concentration $CF_{HbO2}$, a deoxygenated hemoglobin concentration $C_{Hb}$, a total hemoglobin concentration $C_{tHb}$, and a degree of tissue oxygen saturation $SO_2$ calculated from results of FIGS. 6(a) and 6(b). Also, numeric numbers written to FIG. 6 indicate (Average value)±(Standard deviation).

Referring to FIG. 6, it can be seen that the standard deviation of the numerical value obtained by the measurement device 1A and the measurement method of the present embodiment is significantly smaller than the standard deviation of the numerical value of the comparative example. From this fact, it can be seen that the accuracy of calculation of the reduced scattering coefficient and absorption coefficient is improved according to the measurement device 1A and the measurement method of the present embodiment.

FIGS. 7 and 8 are tables illustrating change coefficient values of the absorption coefficient, the reduced scattering coefficient, and the hemoglobin amount (the total hemoglobin concentration $C_{tHb}$ and the degree of tissue oxygen saturation $SO_2$) obtained by changing the measurement time during the forehead measurement from 100 ms to 5000 ms. FIG. 7 illustrates a change coefficient value obtained by the conventional method and FIG. 8 illustrates a change coefficient value obtained by the measurement device 1A and the measurement method of the present embodiment. The reduced scattering coefficient ratio $R_1:R_2:R_3$ is the same as above. Normally, the change coefficient value decreases as the measurement time increases (that is, the measurement accuracy increases), but the change coefficient value is smaller than that of the conventional method if a comparison is performed during the same measurement time in the measurement device 1A and the measurement method of the present embodiment as is apparent from the comparison between FIGS. 7 and 8. In other words, it is possible to shorten a measuring time for obtaining certain measurement accuracy according to the measurement device 1A and the measurement method of the present embodiment.

Figure 9:
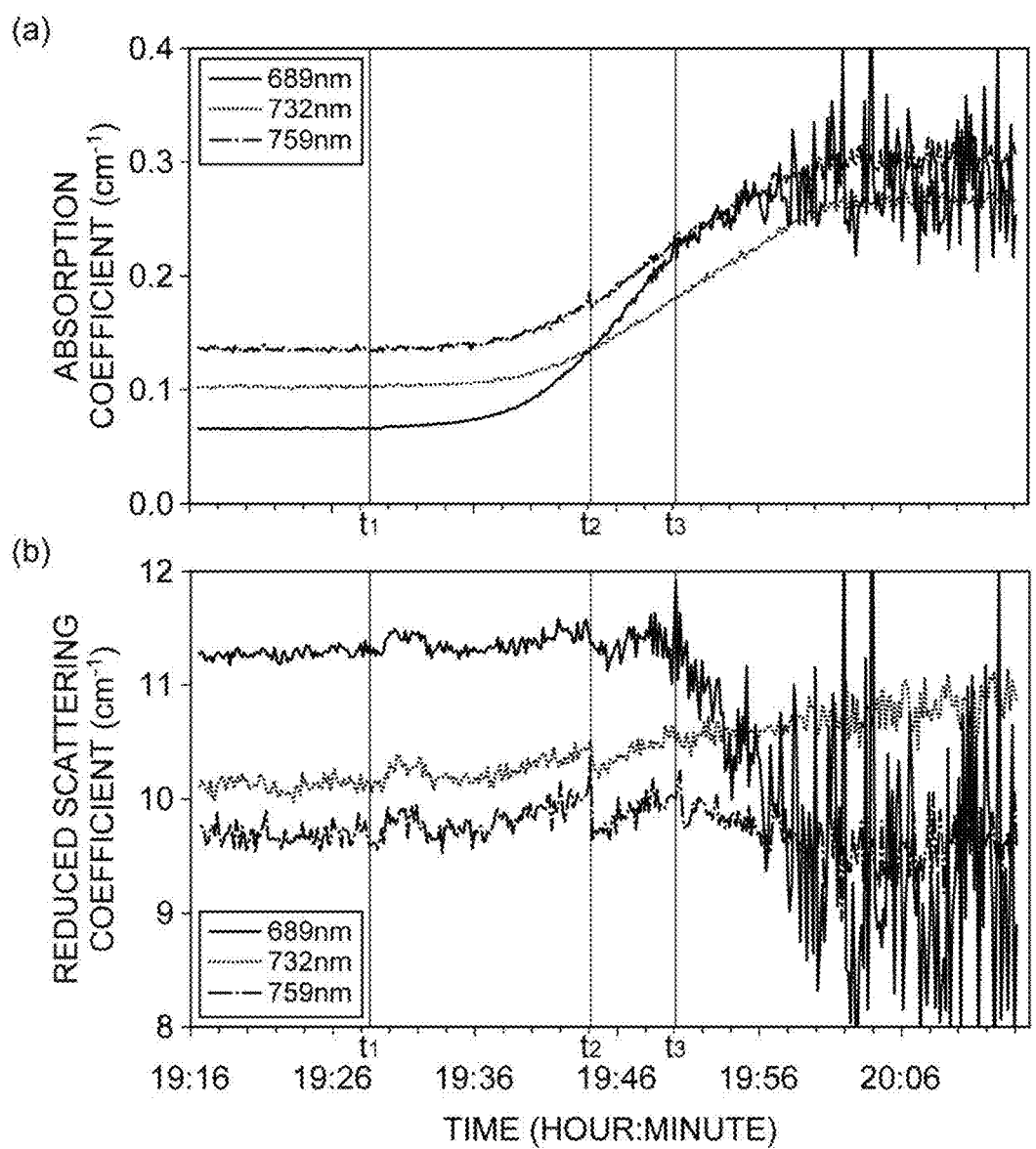
FIG. 9 is a graph illustrating results of measuring an absorption coefficient and a reduced scattering coefficient of each wavelength using a blood phantom.
Figure 10:
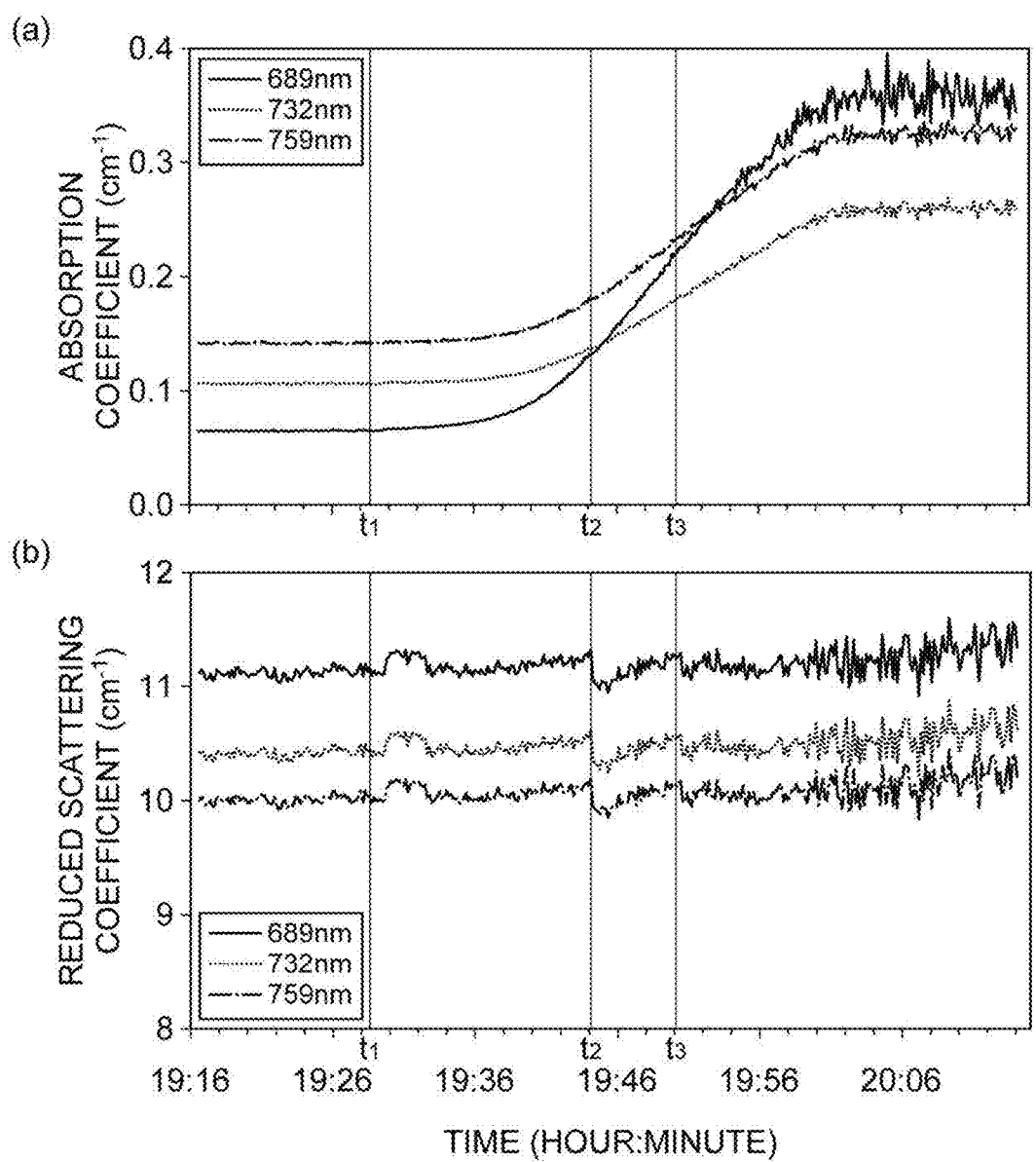
FIG. 10 is a graph illustrating results of measuring an absorption coefficient and a reduced scattering coefficient of each wavelength using a blood phantom.

FIGS. 9 and 10 are graphs illustrating results of measuring absorption coefficients and reduced scattering coefficients for wavelengths (689 nm, 732 nm, and 759 nm) by using a blood phantom. In FIGS. 9 and 10, the horizontal axis represents time, and the vertical axis represents an absorption coefficient (unit: $cm^{-1}$) and a reduced scattering coefficient (unit: $cm^{-1}$). Also, FIG. 9 illustrates the results based on the conventional method, and FIG. 10 illustrates the results based on the measurement device 1A and the measurement method of the present embodiment. In FIGS. 9 and 10, time $t_1$ indicates a timing at which dry yeast for consumption of oxygen in the blood phantom is applied, time $t_2$ indicates a timing at which an attenuator is changed, and time $t_3$ indicates a timing at which the attenuator is further changed.

Figure 11:
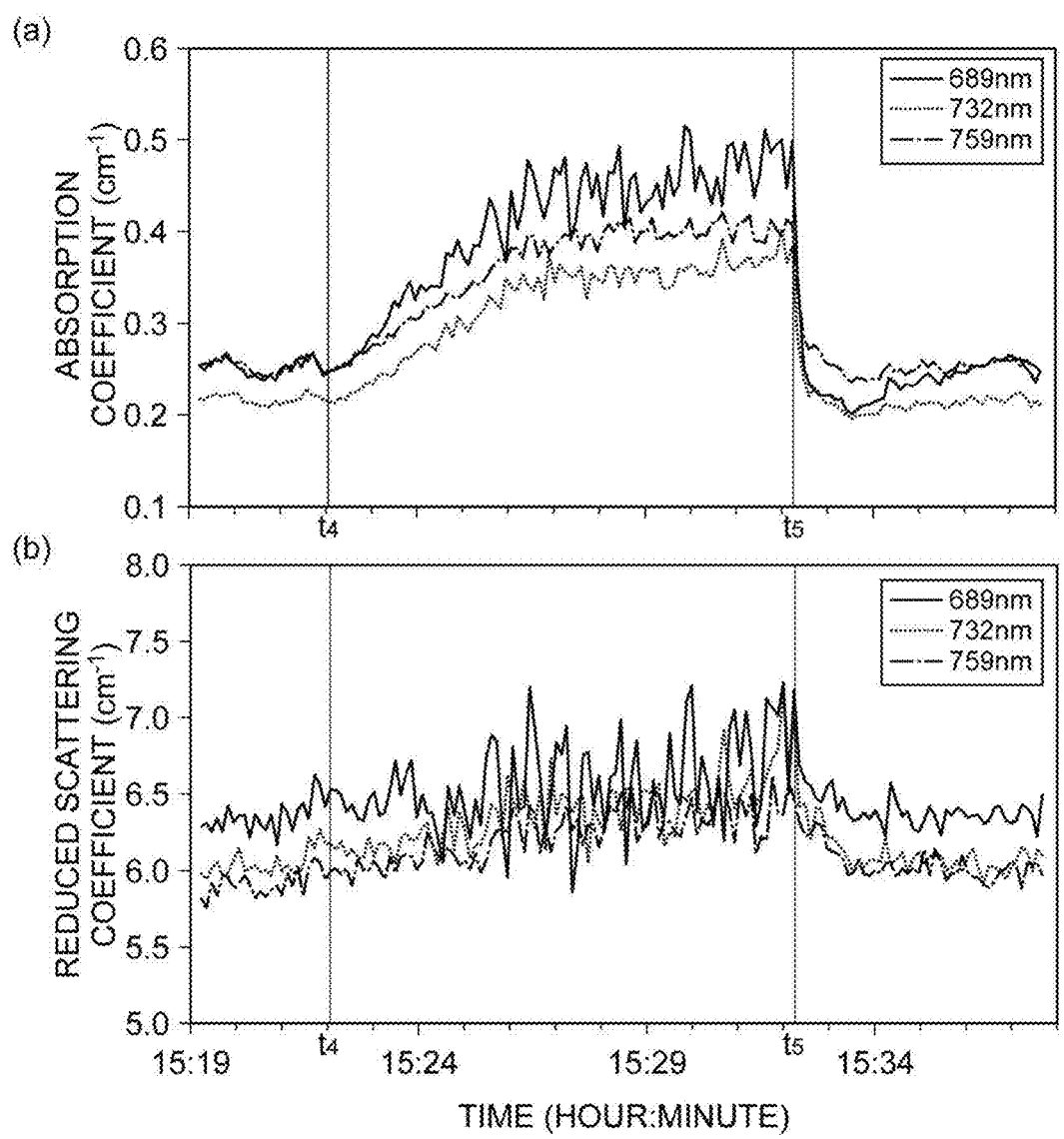
FIG. 11 is a graph illustrating results of measuring an absorption coefficient and a reduced scattering coefficient of each wavelength of a human forearm portion.

Also, FIGS. 11 and 12 are graphs illustrating results of measuring absorption coefficients and reduced scattering coefficients for wavelengths (689 nm, 732 nm, and 759 nm) of the human forearm portion. In FIGS. 11 and 12, the horizontal axis represents time and the vertical axis represents an absorption coefficient (unit: $cm^{-1}$) and a reduced scattering coefficient (unit: $cm^{-1}$). Also, FIG. 11 illustrates results based on the conventional method and FIG. 12 illustrates results based on the measurement device 1A and the measurement method of the present embodiment. In FIGS. 11 and 12, time $t_4$ indicates a timing at which a cuff is attached to the forearm portion and time $t_5$ indicates a timing at which the cuff is removed.

In the measurement using the blood phantom illustrated in FIGS. 9 and 10, the degree of tissue oxygen saturation $SO_2$ ranges from 0% to 100% in a wide range, unlike a living body. Accordingly, the S/N ratio tends to be lower than that of the living body. Also, in the measurement of the forearm portion illustrated in FIGS. 11 and 12, the absorption coefficient of 689 nm is abruptly increased by attaching a cuff and giving abrupt change (deoxygenation) to the amount of hemoglobin, and the S/N ratio is reduced. Referring to FIGS. 9 to 12, in comparison with the conventional method (FIGS. 9 and 11), even in the state where the S/N ratio is low as described above, it can be seen that the amplitude of the graph is small and the measurement can be stably performed with high accuracy in the measurement device 1A and the measurement method of the present embodiment (FIGS. 10 and 12). Thereby, it is also possible to shorten the measurement time.

INDUSTRIAL APPLICABILITY

According to the scattering absorber measurement device and the scattering absorber measurement method based on the aspects of the present invention, it is possible to accurately calculate a reduced scattering coefficient and an absorption coefficient.

REFERENCE SIGNS LIST

1A Scattering absorber measurement device
2 Optical fiber holder
5 Computation unit
9 Display unit
10 Control unit
31 Light source unit (light source)
32 Light irradiation fiber
41 Light detection unit (photodetector)
42 Light detection fiber
51 Signal processing unit
52 Optical characteristic measurement unit
53 Reduced scattering coefficient database
54 Computation processing unit
B Scattering absorber
D Light detection position
P(n) Light pulse
S Light input position

The invention claimed is:

1. A scattering absorber measurement device comprising:
a light source configured to output a plurality of light pulses having different wavelengths input to a scattering absorber;
a photodetector configured to detect each light pulse propagating inside the scattering absorber and outputting a detection signal; and
a computation unit having a processor and configured to calculate reduced scattering coefficients and absorption coefficients according to a time-resolved spectroscopic measurement method on the basis of the detection signal,
wherein the computation unit determines data related to ratios of reduced scattering coefficients among wavelengths of the plurality of light pulses $R_1:R_2: \ldots :R_N$, and calculates the reduced scattering coefficients and the absorption coefficients by fitting a light diffusion equation in which the reduced scattering coefficients are assumed as products $R_1 \cdot \mu'_{s,R}, R_2 \cdot \mu'_{s,R}, \ldots, R_N \cdot \mu'_{s,R}$ of the ratios $R_1:R_2: \ldots :R_N$ and a basic reduced scattering coefficient $\mu'_{s,R}$ with respect to time-resolved measurement profiles in the wavelengths based on the detection signal.

2. The scattering absorber measurement device according to claim 1, wherein the computation unit performs weighting based on the time-resolved measurement profile of each wavelength with respect to the reduced scattering coefficient of each wavelength used in the fitting.

3. The scattering absorber measurement device according to claim 1, further comprising:
a storage device configured to store the data related to the ratios of the reduced scattering coefficients among the wavelengths of the plurality of light pulses.

4. A scattering absorber measurement method comprising the steps of:

inputting a plurality of light pulses having different wavelengths to a scattering absorber;
detecting each light pulse propagating inside the scattering absorber and outputting a detection signal;
determining data related to a ratio of reduced scattering coefficients among wavelengths of the plurality of light pulses; and
calculating reduced scattering coefficients and absorption coefficients according to a time-resolved spectroscopic measurement method on the basis of the detection signal,
wherein the reduced scattering coefficients and the absorption coefficients are calculated by fitting a light diffusion equation in which the reduced scattering coefficients are assumed as products $R_1 \cdot \mu'_{s,R}$, $R_2 \cdot \mu'_{s,R}, \ldots, R_N \cdot \mu'_{s,R}$ of the ratios $R_1:R_2:\ldots:R_N$ and a reduced scattering coefficient $\mu'_{s,R}$ with respect to time-resolved measurement profiles in the wavelengths based on the detection signal.

5. The scattering absorber measurement method according to claim 4, wherein weighting based on the time-resolved measurement profile of each wavelength is performed with respect to the reduced scattering coefficient of each wavelength used in the fitting in the calculating step.

6. The scattering absorber measurement method according to claim 4, wherein the data related to the ratio of the reduced scattering coefficients among the wavelengths of the plurality of light pulses is stored in a storage device.

* * * * *